(12) United States Patent
Chang et al.

(10) Patent No.: US 9,594,293 B2
(45) Date of Patent: Mar. 14, 2017

(54) METHOD AND APPARATUS FOR UNIFORMLY FOCUSED RING LIGHT

(71) Applicant: OG Technologies, Inc., Ann Arbor, MI (US)

(72) Inventors: Tzyy-Shuh Chang, Ann Arbor, MI (US); Changhung Lin, Ypsilanti, MI (US); Hsun-Hau Huang, Ann Arbor, MI (US)

(*) Notice: Subject to any disclaimer, the term of this patent is extended or adjusted under 35 U.S.C. 154(b) by 0 days.

(21) Appl. No.: 15/019,002

(22) Filed: Feb. 9, 2016

(65) Prior Publication Data

US 2016/0154292 A1 Jun. 2, 2016

Related U.S. Application Data

(62) Division of application No. 14/073,455, filed on Nov. 6, 2013.

(60) Provisional application No. 61/789,037, filed on Mar. 15, 2013, provisional application No. 61/726,964, filed on Nov. 15, 2012.

(51) Int. Cl.

| | |
|---|---|
| *G01J 1/04* | (2006.01) |
| *G01N 21/47* | (2006.01) |
| *G01B 11/24* | (2006.01) |
| *G01B 11/14* | (2006.01) |
| *H04N 5/228* | (2006.01) |
| *G03B 15/06* | (2006.01) |
| *H04N 5/225* | (2006.01) |
| *G01N 21/88* | (2006.01) |

(52) U.S. Cl.
CPC ......... *G03B 15/06* (2013.01); *G01N 21/8806* (2013.01); *H04N 5/2256* (2013.01); *G01N 2201/0636* (2013.01); *G03B 2215/0575* (2013.01); *H04N 2005/2255* (2013.01)

(58) Field of Classification Search
CPC ............ G01N 21/952; G01N 21/8806; G01N 2021/8918; G01N 2021/8812; G01B 11/24; G01B 11/2513; G01B 11/08; G03B 2215/0575
USPC ....... 356/606, 601, 635, 446, 236, 614, 638, 356/639, 640; 382/141, 154, 165; 348/222.1, E5.029
See application file for complete search history.

(56) References Cited

U.S. PATENT DOCUMENTS

| | | |
|---|---|---|
| 6,542,249 B1 | 4/2003 | Kofman et al. |
| 7,630,537 B2 | 12/2009 | Sato et al. |
| 7,808,644 B2 | 10/2010 | Wagner |
| 8,306,308 B2 | 11/2012 | Choi et al. |

(Continued)

FOREIGN PATENT DOCUMENTS

| | | | | |
|---|---|---|---|---|
| JP | 2009039199 | * | 2/2009 | ............. G02B 23/24 |
| WO | 2013116299 A1 | | 8/2013 | |

OTHER PUBLICATIONS

Sun, et al., Motion Deviation Rectifying Method of Dynamically Measuring Rail Wear Based on Multi-Line Structured-Light Vision, Optics & Laser Technology 50 (2013) 25-32.

(Continued)

*Primary Examiner* — Sunghee Y Gray (57) ABSTRACT

An apparatus and method for the function to control the lighting direction onto an object surface, focus the light, and maintain the lighting uniformity. A ring light system takes advantage of a contoured reflector to match with the uniform, non-focused ring light source, and converting the non-focused ring light source into a focused uniform ring light source.

2 Claims, 4 Drawing Sheets

(56) References Cited

U.S. PATENT DOCUMENTS

| | | |
|---|---|---|
| 8,390,826 B2 | 3/2013 | Walstra |
| 8,592,768 B1 * | 11/2013 | Djeu .................. G01N 21/3151 250/339.12 |
| 2007/0296956 A1 * | 12/2007 | Haugholt ................ G01M 3/38 356/51 |
| 2011/0270562 A1 | 11/2011 | Ito et al. |
| 2013/0202727 A1 | 8/2013 | Kitazawa et al. |

OTHER PUBLICATIONS

Kumar, et al., Single Frame Digital Fringe Projection Profilometry for 3-D Surface Shape Measurement, Optik 124 (2013) 166-169.

* cited by examiner

METHOD AND APPARATUS FOR UNIFORMLY FOCUSED RING LIGHT

CROSS-REFERENCE TO RELATED APPLICATIONS

This application is a divisional of U.S. patent application Ser. No. 14/073,455 filed 6 Nov. 2013, which claims the benefit of U.S. provisional application No. 61/726,964, filed 15 Nov. 2012 (the '964 application), and U.S. provisional application No. 61/789,037, filed 15 Mar. 2013 (the '037 application). The '964 application and the '037 application are both hereby incorporated by reference as though fully set forth herein.

BACKGROUND a. Technical Field

The instant disclosure relates generally to a method and apparatus for illuminating an object, which may be an elongated object such as a pipe, bar, tube, wire, rod, or the like, for use in imaging applications.

b. Background

This background description is set forth below for the purpose of providing context only. Therefore, any aspects of this background description, to the extent that it does not otherwise qualify as prior art, is neither expressly nor impliedly admitted as prior art against the instant disclosure.

Lighting, particularly uniform lighting intensity is very important to imaging applications such as surface defect inspection. There are various types of lighting designs to accomplish such uniformity. For instance, a light homogenizer (e.g., typically a square or hexagon rod lens) can be used to distribute a non-uniform light beam into a uniform light beam over a two-dimensional (2D) area. This approach supports the uniform lighting over a flat surface.

Another approach is known as cloudy-day illumination. Automatic inspection of objects of interest (e.g., rod, bar, wire, etc.) is very common today. These objects are typically in round and long (i.e., have a circular shape in radial cross-section and are elongated). For instance, a plastic water pipe can be 10 meters long at a diameter of roughly 20 mm. An electrical wire is also subject to inspection to ensure that the insulation is properly applied. Commercially available systems for inspection of such elongated objects typically employ optical systems employing cloudy-day illumination techniques. The object to be inspected may typically be moving in its axial direction-along a longitudinal axis— while the imaging devices are arranged to image the circumference of the object as the object moves through the optical system. Multiple light sources are in use to project the light onto the object surface from all kinds of directions. This approach, however, has restrictions. First, it is limited in light intensity to that which is reflected back from the object, unless very high power light sources are used. The limited reflected light intensity results in a limited scanning rate, as well as a limited optical resolution (i.e., lower scanning rate, less resolution; or higher resolution optics typically darker). Second, the diffused lighting cannot support a fast object moving speed. Third, the light projection direction is not controlled and thus cannot be used to emphasize certain defects by selection of designed incident angles.

In addition, other approaches are known that can be used for imaging moving elongated objects, as seen by reference to U.S. Pat. No. 6,950,546, which discloses use of multiple line lights with individual light boosters, where each line light may be adjustable to form a uniform ring. Still other approaches are known, such as using directional projected spot lights along the circumference of an object.

However, objects with highly reflective outer surfaces present very challenging imaging situations. For example, processed metal objects are typically very shiny, and have mirror like reflection properties. As a result, even a segmented approach (e.g., individual line lights) may result in uniform stripes in the captured image.

Using a true optical fiber ring light, which can have a large number of fine light guides arranged over a circle, could possibly address the above-mentioned problem. However, the light, as coming out of a light guide, has a fan angle (i.e., the angle that is associated with the total reflection, or the refraction index of the light guide material; the fan angle may typically be about a 60° solid angle if the light guide is glass). Unfortunately, it is very difficult to focus the ring of light emanating from such a ring light without interruption to the uniformity.

The foregoing discussion is intended only to illustrate the present field and should not be taken as a disavowal of claim scope.

SUMMARY

In an embodiment, an illumination assembly is provided for use in an inspection system, wherein the inspection system is configured to illuminate an elongated object extending along a longitudinal axis. The illumination assembly includes a light source, a ring light, and a reflector. The light source is configured to produce a light output. The ring light has a central aperture through which the longitudinal axis passes and in which the object is disposed. The ring light is coupled to receive the light output from the light source and output a ring of light. In an embodiment, the ring of light may be generally a cone shape. The reflector has an annular body with a contoured reflective surface that is configured to focus and direct the ring of light from the ring light onto a circumference of the object to form an illuminated light band. In an embodiment, the illuminated light band may be on and around the circumference of the object. The illuminated light band has a predetermined width (i.e., axial width or width taken in an axial direction) and a substantially uniform light intensity over the predetermined width. In an embodiment, an axial cross-section through the contoured reflective surface of the reflector defines a segment of a circular arc having a predetermined radius.

In an embodiment, a system is provided for imaging an elongated object extending along a longitudinal axis. The system includes an illumination assembly, an image acquisition assembly, and a computing unit. The illumination assembly is configured to illuminate the object to form an illuminated light band on an outer circumference of the object. The illumination assembly includes a light source, a ring light, and a reflector. The light source is configured to produce light output. The ring light has a central aperture through which the longitudinal axis passes and in which the object is disposed. The ring light is coupled to receive the light output from the light source and output a ring of light. In an embodiment, the ring of light is in the general shape of a cone. The reflector includes an annular body (i.e., ring like) with a contoured reflective surface configured to focus and direct the ring of light from the ring light onto the circumference of the object to form an illuminated light band. The illuminated light band has a first predetermined axial width and further has a substantially uniform light intensity over the first predetermined axial width. The image acquisition assembly has a field of view configured to image a second predetermined axial width over the circumference of the object to define an image band and produce image data corresponding thereto. The image acquisition assembly is arranged relative to the illumination assembly so that the image band is within the illuminated light band. The computing unit is coupled to the image acquisition assembly and is configured to receive and process the image data for identifying predetermined surface features of the object.

The foregoing and other aspects, features, details, utilities, and advantages of the present disclosure will be apparent from reading the following description and claims, and from reviewing the accompanying drawings.

DETAILED DESCRIPTION

Embodiments of a ring light system 10 (hereinafter an illumination assembly 10) described herein may be used to illuminate an object 30 (see FIG. 1) for imaging purposes wherein object 30 may be an elongated (i.e., commonly referred to as long products in the steel industry), axially symmetric object (i.e., an object that is symmetric about an axis when a radial cross-section is considered). For example only, such objects may have cross-sectional shapes including but not limited to a round shape, an oval shape, a hexagonal shape, an octagonal shape, a square shape, and the like. The object may be substantially continuous in the longitudinal extent for at least a predetermined distance. For such objects, it is required for imaging that the lighting be focused and be substantially uniform in intensity. Embodiments of illumination assembly 10 can be advantageously used to illuminate object 30 to support imaging applications on the object surface, and may be used to illuminate highly reflective (i.e., "shiny") object surfaces, such as found, for example, with processed metal objects.

As described in the Background, one can make a special circular booster lens for use with a fiber ring light to achieve uniform light intensity. Further, focusing is also generally necessary to boost the magnitude of the light intensity to support not only the high object moving speed (e.g., such as 10 m/s or faster) that can be expected in some production environments, but also to support high imaging rates, as well as allow for the selection and use of a precise designed incident angle (i.e., desired to emphasize certain surface defects on some kinds of objects 30). In light of these considerations, it is desirable to have an illumination assembly that can not only control the direction of the lighting onto the object surface, but one that can also focus the light (i.e., to increase the magnitude of the light intensity) while also maintaining the uniformity of the light intensity. The instant disclosure describes an embodiment of an illumination assembly having a reflector that features a contoured circular reflective surface, where the contoured reflective surface is configured for focusing and reflecting light onto the object surface without compromising uniformity.

Figure 1:
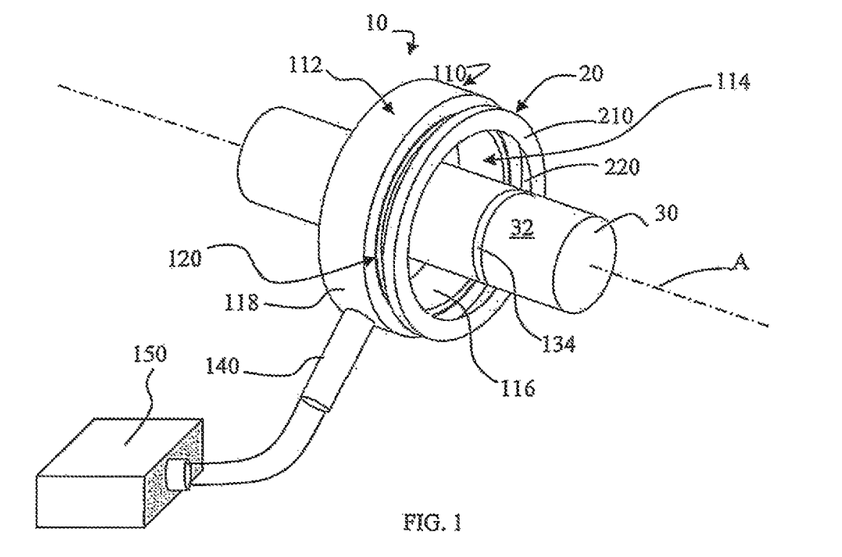
FIG. 1 is an isometric view of a first embodiment of a ring light.

FIG. 1 is an isometric view of an embodiment of an illumination assembly 10 for use in an imaging system 12 (best shown in FIG. 7) that is configured to illuminate an elongated object 30 extending along a longitudinal axis designated "A". Illumination assembly 10 may include a light source 150 configured to produce a light output, a ring light 110 coupled to light source 150 configured to receive the light output from light source 150 and output a uniform but diffused ring of light 130, and a reflector 20 configured to receive and focus ring of light 130 into a uniform ring of focused light 132 (best shown in FIGS. 4A and 7) and direct ring of focused light 132 around the circumference of object 30, to thereby form an illuminated light band 134. Illuminated light band 134 is characterized by (i) a designed incident angle, (ii) an increased magnitude of the light intensity by virtue of its focusing functionality, and (iii) a substantially uniform light intensity across its width. Illuminated light band 134 can be imaged using known imaging apparatuses (e.g., surface imaging and inspection), for example, like the imaging apparatus described in U.S. application Ser. No. 10/331,050, filed 27 Dec. 2002 (the '050 application), now U.S. Pat. No. 6,950,546, and/or U.S. application Ser. No. 12/236,886, filed 24 Sep. 2008 (the '886 application), now U.S. Pat. No. 7,627,163. The '050 application and the '886 application are both hereby incorporated by reference as though fully set forth herein. For example only, embodiments of illumination assembly 10 described herein may be used in substitution of, or in combination with, the illumination mechanism(s) described in the '050 application and the '886 application. A brief description of an exemplary imaging system that can be used in connection with illumination assembly 10 will now be set forth in connection with FIG. 7.

Figure 7:
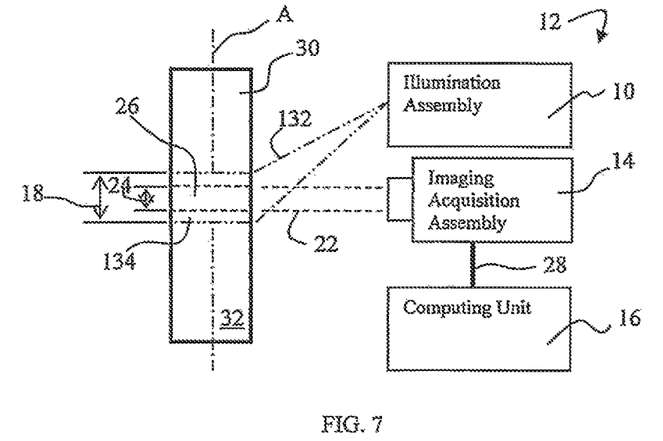
FIG. 7 is diagrammatic and block diagram view of a system for imaging an object including an image acquisition assembly and computing unit used in conjunction with an illumination assembly embodiment.

FIG. 7 is a diagrammatic and block diagram view of a system 12 for imaging elongated object 30 extending along longitudinal axis "A". Imaging system 12 can use embodiments of illumination assembly 10. Imaging system 12 may comprise known imaging or inspection system components (e.g., as set forth above, and as disclosed in the '050 and '886 applications, incorporated by reference). In the illustrated embodiment, imaging system 12 may include an embodiment of illumination assembly 10, an image acquisition assembly 14 and a computing unit 16. As described above, illumination assembly 10 directs focused light ring 132 onto the outer surface 32 of object 30 to form illuminated light band 134 having uniform light intensity. In an embodiment, illuminated light band 134 is substantially uniform in light intensity over at least a first predetermined axial width 18.

Image acquisition assembly 14 has a field of view, designated 22, configured to image a second predetermined axial width 24 over and around the complete circumference of object 30 to define an image band 26. Image acquisition assembly 14 is further configured to produce image data 28 corresponding to the acquired one or more image band(s) 26 as object 30 moves along axis "A". In an embodiment, image acquisition assembly 14 may include plural line scan cameras (not shown) arranged around the circumference at predetermined angular positions configured to fully image around the entire circumference of object 30 (i.e., the image band corresponds to 360 degrees around the circumference of object 30). In addition, image acquisition assembly 14 is arranged relative to illumination assembly 10 such that image band 26 is positioned within illuminated light band 134. This relative arrangement ensures that image acquisition assembly 14 is imaging uniformly illuminated portions of the outer surface 32 of object 30.

Computing unit 16 is coupled to image acquisition assembly 14 to receive image data 28 and process image data 28 for identifying predetermined surface features of object 30. For example, predetermined surface features may include various surface defects. In addition, computing unit 16 may be configured to combine image data 28 corresponding to a plurality of image bands 26 so as to form a complete image of the outer surface 32 of object 30 along a predetermined axial length of object 30. Computing unit 16 may be configured to perform other functions, such as set forth in the '050 and '886 applications incorporated by reference.

Figure 2:
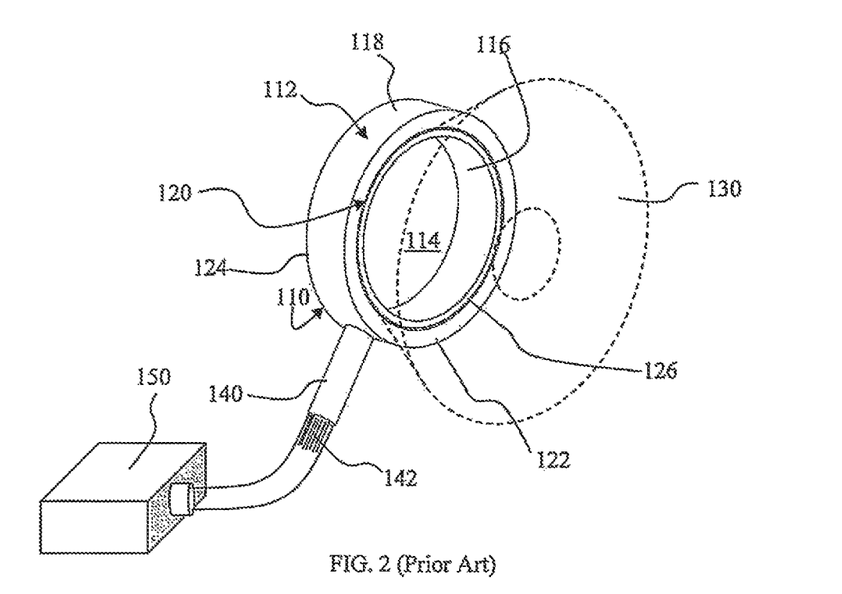
FIG. 2 is an isometric view of a conventional ring light source (non-focused).

With reference to FIGS. 1-2, ring light 110 may comprise conventional components known to those of ordinary skill in the art. In an embodiment, ring light 110 may comprise a ring-shaped hub 112, referred to hereinafter as a ring housing 112, which includes a central aperture 114 defined in part by an inside diameter (ID) portion 116 and through which longitudinal axis "A" passes. Central aperture 114 is configured in size (Le., diameter) and shape so as to accommodate object 30 passing therethrough. It should be understood that the ring shape (i.e., circular) of ring housing 112 is exemplary only, and not limiting in nature. For example only, ring housing 112 may be configured in alternate shapes, limited only by the ability of object 30 to pass through its central aperture 114.

Ring housing 112 further includes an outside diameter (OD) portion 118, a light emitting ring 120 formed in a first, axially-facing end surface 122, and a second, axially-facing end surface 124 opposite first, axially-facing surface 122. Light emitting ring 120 is defined, in part, by a circular-shaped optical window 126 formed in first, axially-facing end surface 122. In an embodiment, optical window 126 may be a circular aperture.

Figures 3A, 3B, 3C:
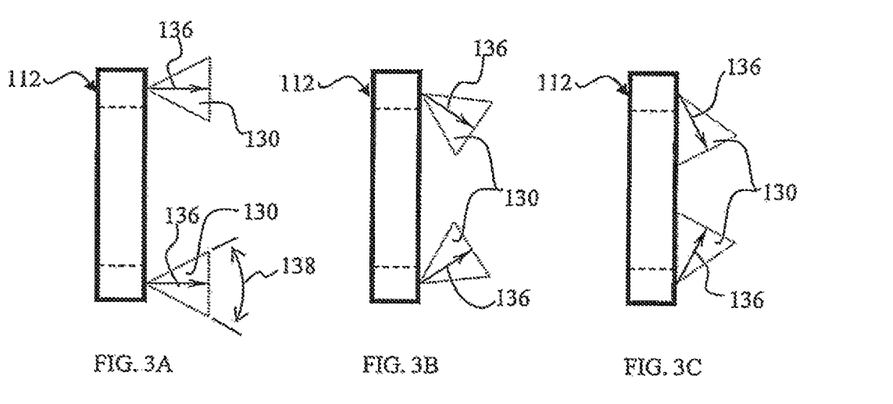
FIGS. 3A-3C are side views illustrating a number of conventional ring light emission angles.

In an embodiment, light source 150 produces a light output that is provided to a light guiding bundle 140. In this regard, light guiding bundle 140 includes a proximal end that is coupled to light source 150 and a distal end that is coupled to ring housing 112 of ring light 110. Additionally, light guiding bundle 140 includes a plurality of optical fibers, referred to herein as optical fiber light guides 142. In an embodiment, light emitting ring 120 may be formed by the plurality of optical fiber light guides 142, which are fed into ring housing 112. The respective ends of optical fiber light guides 142 are arranged uniformly along light emitting ring 120, which, in the illustrated embodiment, may be in the shape of a circle. The ends of optical fiber light guides 142 (i.e., collectively referred to as light emitting ring 120) may be optically polished to have an improved light emitting effect from the fiber ends. The fiber ends can be arranged to have an angle of emission 136, as illustrated in FIGS. 3A-3C showing various angles of emission.

Without loss of generality, in an embodiment, light emitting ring 120 may emit a ring of light 130 such that the angle of emission 136 is perpendicular to first, axially-facing end surface 122, as shown in FIG. 2.

As already described above, light source 150 generates a light output for illumination assembly 10. Light source 150 may include conventional components known in the art for generating such light, such as a bulb or a light-emitting diode (LED) or similar light emitting source(s). In the illustrated embodiment, the light output from light source 150 is typically focused into proximal ends of the optical fiber light guides 142 at the proximal end of light guiding bundle 140.

In an embodiment, optical fiber light guides 142 contained inside light guiding bundle 140 may be (typically) mixed up along the length of light guiding bundle 140 so that the distal ends of optical fiber light guides 142 are randomly arranged to achieve the best uniformity at light emitting ring 120. It should be understood, however, that such randomization is not necessary. Other approaches, such as placing a homogenizer before sending the light into light guiding bundle 140, may result in the desired uniformity. Light emitted by light emitting ring 120 is, unless focused, diffused into a ring of light 130, which may take the shape of a cone due to the fan angle associated with each end of the optical fiber light guides 142.

While an embodiment of ring light 110 has been set forth above, those of ordinary skill in the art will know that ring light 110 may be formed in a different ways (i.e., different embodiments). For instance, light emitting ring 120 may alternatively comprise an array of LEDs (not shown) arranged in a ring shape. In such an embodiment, a diffusing plate (not shown) may be placed in front of light emitting ring 120 to smear the individual LED light beams to generate a uniform light intensity ring of light 130. In a further embodiment, light emitting ring 120 may alternatively comprise a circular fluorescent tube. In this case, ring light 110 itself will be the light source and thus there will be no need for either light source 150 or light guiding bundle 140. Note that both LEDs and fluorescent tubes have light emitting angles as illustrated by the diffused ring of light 130, which takes the general shape of a cone. In sum, ring light 110 produces a uniform intensity, but diffused, ring of light 130, characterized by angle of emission 136.

Figure 4:
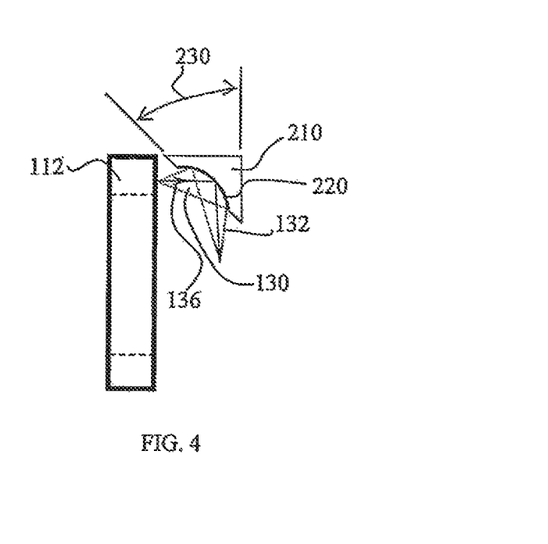
FIG. 4 is a cross-sectional, diagrammatic view of the ring housing in relation to the reflector.
Figure 5A:
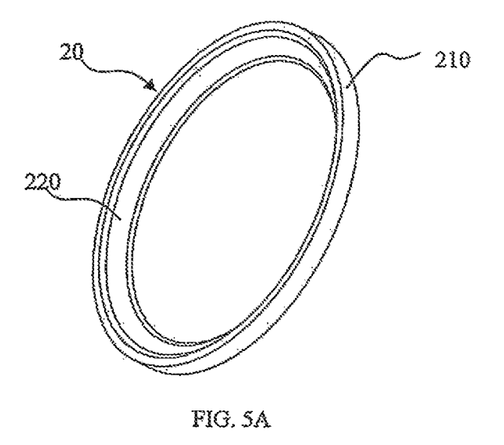
FIG. 5A is an isometric view of a reflector of the ring light of FIG. 1.
Figure 5B:
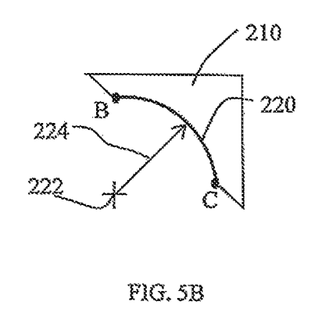
FIG. 5B is an enlarged, cross-sectional view of the reflector.

Referring now to FIGS. 4-5B, to accomplish the light focusing (i.e., increases magnitude of light intensity) and directing (i.e., adjusts direction) functions, reflector 20 is configured to include a contoured reflective surface. In an embodiment, reflector 20 can be a ring part (best shown in FIG. 5A), having an annular reflector body 210 with a contoured reflective surface 220. Reflector 20 is disposed adjacent to ring housing 112, whereby contoured reflective surface 220 is positioned adjacent to and facing first, axially-facing end surface 122. In an embodiment (FIG. 5B), an axial cross-section of contoured reflective surface 220 comprises a segment of a concave arc, such as a circular arc. The circular arc is taken with reference to a circular center 222 and which has a predetermined radius 224. As also shown in FIG. 5B, the segment of the contoured reflective surface 220 includes a pair of endpoints B, C, which when viewed in axial cross-section, forms a chord BC therebetween.

Contoured reflective surface 220 is configured to be highly reflective. For example, contoured reflective surface 220 can be a highly polished metal surface, or a surface with a highly reflective coating. Those skilled in the art shall know other approaches of creating a contoured reflective surface. An example of such highly reflective material is stainless steel or copper or bronze. An example of such highly reflective coating is chrome plating, on a substrate made of steel.

The contoured (i.e., light direction changing) reflective surface 220 is configured to focus the uniform (but diffused) ring of light 130 without compromising the uniformity (i.e., no interruption to the focusing device). As shown in FIG. 4, the ring of light 130 is received, focused, and directed into a focused ring of light 132. The focusing function increases the magnitude of the light intensity. As described above, the ring of light 130 emitted by light emitting ring 120 is diffused into a cone shape. The diffused ring of light 130 is captured by the contoured reflective surface 220, which may have a designed shape to focus uniform (but diffused) ring of light 130 into focused ring of light 132. The shape of contoured reflective surface 220 determines the focal distance of focused ring of light 132, whereas an angle 230 that reflector body 210 takes relative to ring housing 112 determines a projection angle of focused ring of light 132. In other words, contoured reflective surface 220 can be configured with a characteristic focusing distance and direction relative to the curve of contoured reflective surface 220. However, even with the optical properties of contoured reflective surface 220 being established, the pointing direction of focused ring of light 132 can be further adjusted via variation of the angle 230 at which reflector body 210 is disposed relative to ring housing 112.

With continued reference to FIG. 4, the orientation of contoured reflective surface 220 relative to ring of light 130, which controls the pointing direction of the focused ring of light 132, can be further described as follows. Note that ring of light 130 that is output from light emitting ring 120 has an axis of emission 136, which is also shown for various angles in FIGS. 3A-3C. As described in connection with FIG. 5B, contoured reflective surface 220 corresponds in shape to a portion of a surface of a sphere having a center point (i.e., center point 222—FIG. 5B) with a predetermined radius (i.e., radius 224—FIG. 5B). A chord (i.e., chord BC—FIG. 5B) may be therefore defined between the endpoints of a span of an arc taken with respect to an axial cross-section of the contoured reflective surface 220. Reflector 20 can be arranged such that the chord (i.e., the chord BC—FIG. 5B) forms a predetermined angle with the axis of emission 136. In an embodiment, the predetermined angle between the axis of emission 136 and the chord BC may be adjustable so as to alter the pointing direction of focused ring of light 132. Altering the pointing direction can cause a corresponding change in the axial position of illuminated light band 134 on object 30 (i.e., how much of an axial offset or distance between the ring housing and the illuminated light band). In addition, altering the pointing direction can have beneficial effects for illuminating certain kinds of surface defects.

In an embodiment, contoured reflective surface 220 may be a segment of a circular arc of a certain diameter, as already described above. In an alternate embodiment, contoured reflective surface 220 may be a segment of a parabolic arc of certain a/b axial lengths, or a segment of any designed concave arc based on the principle of light reflection. For example only, a parabola may be defined by $y=ax^2+bx+c$, wherein contoured reflective surface 220 can correspond to a segment of such a parabola, wherein the focusing characteristics of the parabola segment can be tuned to meet the requirements of any particular application.

Referring again to FIG. 1, when the respective diameters of reflector body 210 and contoured reflective surface 220 are matched properly with light emitting ring 120, the combination results in an illumination assembly 10 that is capable of surrounding and illuminating the outer surface 32 of object 30 around its entire circumference to thereby define illuminated light band 134. Illuminated light band 134 is well focused at a desired projection angle and which is substantially uniform in intensity both across its axial width as well as along and around the circumference of object 30.

In operation, object 30 may be moved via external apparatus longitudinally along longitudinal axis "A" through central aperture 114 of ring light 110 and reflector 20. The uniform (but diffused) ring of light 130 emitted from light emitting ring 120 is captured by reflector 20 and is focused and directed by contoured reflective surface 220 onto the outer surface 32 of object 30 around its entire circumference-resulting in a uniformly illuminated (light intensity) light band 134. The axial offset location of illuminated light band 134 on object 30 (relative to ring housing 112) is controlled by the reflecting angle (i.e., angle 230 in FIG. 4), which also control the angle of incidence onto object 30. The latter feature can be adjusted so as to improve illumination of certain kinds of surface defects. The axial width 18 (FIG. 7) of illuminated light band 134 is controlled by the contour of contoured reflective surface 220.

Figure 6:
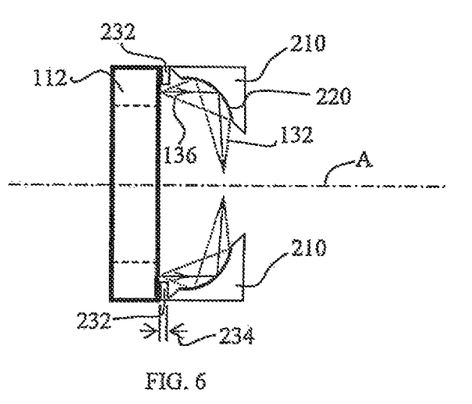
FIG. 6 is a cross-sectional, diagrammatic view of an embodiment of the ring light of FIG. 1, with spacers between the ring housing and the reflector.

FIG. 6 is a diagrammatic, simplified view of a further light ring embodiment similar to that in FIG. 4. In particular, reflector body 210 can be mounted to the ring light 110 (e.g., the ring housing 112) using conventional fasteners (e.g., screws) and one or more spacers 232. Spacers 232 have a thickness 234, taken in the axial direction, for example, in the direction of longitudinal axis "A". In an embodiment, the thickness 234 can be adjusted so as to vary an offset of reflector 20 (and thus also of contoured reflective surface 220) from ring housing 112. The thickness of spacer 232, along with the curvature of contoured reflective surface 220, can be varied to adjust the focusing distance of reflector 20. This adjustment feature can be used to accommodate different diameter/size objects 30.

This novel design is proven to be able to support high speed imaging on objects 30 having mirror light surfaces without any dark stripes. In particular, reflector 20, in embodiments, not only reflects but also functions to focus light so as to achieve substantially uniform illumination on object 30. These features make illumination assembly 10 particularly useful, even on objects 30 with fully or very reflective surfaces.

It should be understood that an imaging system 12, particularly a main electronic control unit (i.e., computing unit 16), as described herein may include conventional processing apparatus known in the art, capable of executing pre-programmed instructions stored in an associated memory, all performing in accordance with the functionality described herein. Such an electronic control unit may further be of the type having both ROM, RAM, a combination of non-volatile and volatile (modifiable) memory so that any software may be stored and yet allow storage and processing of dynamically produced data and/or signals. It should be further understood that the terms "top", "bottom", "up", "down", and the like are for convenience of description only and are not intended to be limiting in nature. While one or more particular embodiments have been shown and described, it will be understood by those of skill in the art that various changes and modifications can be made without departing from the spirit and scope of the present teachings.

The invention claimed is:

1. An illumination assembly for use in an inspection system wherein said assembly is configured to illuminate an elongated object extending along a longitudinal axis, comprising:
   a light source configured to produce light output in the form of a ring light;

said ring light having a central aperture through which the longitudinal axis passes and in which the object is disposed, said ring light being coupled to receive said light output from said light source and output a ring of light;

a reflector having an annular body with a contoured reflective surface configured to focus and direct said ring of light onto a circumference of the object to form an illuminated light band, said illuminated light band having a predetermined axial width and having a substantially uniform light intensity over said predetermined axial width, wherein an axial cross-section of said contoured reflective surface comprises a segment of a circular arc having a predetermined radius, wherein said ring of light output from said ring light has an axis of emission;

wherein said contoured reflective surface of said reflector corresponds in shape to a portion of a surface of a sphere having a center point with a predetermined radius, wherein a chord is defined between endpoints of a span of an arc taken with respect to an axial cross-section of said contoured reflective surface; and wherein said reflector is arranged such that said chord forms a predetermined angle with said axis of emission.

2. The assembly of claim 1 wherein said predetermined angle is adjustable so as to vary an axial offset of said illuminated light band from said ring light.

\* \* \* \* \*